(12) United States Patent
Wang

(10) Patent No.: US 11,771,559 B2
(45) Date of Patent: Oct. 3, 2023

(54) SUPPORT DEVICE AND METHOD OF USING THE SAME

(71) Applicant: Sheng-Peng Wang, Taipei (TW)

(72) Inventor: Sheng-Peng Wang, Taipei (TW)

( * ) Notice: Subject to any disclaimer, the term of this patent is extended or adjusted under 35 U.S.C. 154(b) by 352 days.

(21) Appl. No.: 17/211,940

(22) Filed: Mar. 25, 2021

(65) Prior Publication Data
US 2022/0133481 A1  May 5, 2022

(30) Foreign Application Priority Data
Oct. 30, 2020  (TW) .................. 109137793

(51) Int. Cl.
*A61F 2/28* (2006.01)
*A61F 2/30* (2006.01)

(52) U.S. Cl.
CPC .... *A61F 2/2846* (2013.01); *A61F 2002/2835* (2013.01); *A61F 2002/30224* (2013.01)

(58) Field of Classification Search
CPC .............. A61F 2002/285; A61F 2/2846; A61F 2002/30224
See application file for complete search history.

(56) References Cited

U.S. PATENT DOCUMENTS

| | | | | |
|---|---|---|---|---|
| 2004/0030393 | A1* | 2/2004 | McKay | A61F 2/446 623/17.11 |
| 2005/0273165 | A1* | 12/2005 | Griffiths | A61C 8/0006 606/70 |
| 2012/0296441 | A1* | 11/2012 | Mikhail | A61F 2/2803 623/23.63 |
| 2017/0216033 | A1* | 8/2017 | Daniel | A61F 2/2846 |
| 2018/0221153 | A1* | 8/2018 | Daniel | A61F 2/2803 |
| 2020/0113697 | A1* | 4/2020 | Jania | A61L 27/365 |

FOREIGN PATENT DOCUMENTS

WO    WO-2009092960 A2 *  7/2009 ........... A61B 17/025

* cited by examiner

*Primary Examiner* — Javier G Blanco
(74) *Attorney, Agent, or Firm* — Burris Law, PLLC

(57) ABSTRACT

A support device for supporting a biological membrane includes a support bar that is elongated, that extends along a length direction and that has at least one cylindrical surface extending along the length direction for supporting the biological membrane. A method of using the support device, which is suitable for mounting on a space of a bone defect structure of a human body and which is suitable for supporting a biological membrane, is also disclosed.

9 Claims, 17 Drawing Sheets

SUPPORT DEVICE AND METHOD OF USING THE SAME

CROSS-REFERENCE TO RELATED APPLICATION

This application claims priority of Taiwanese Patent Application No. 109137793, filed on Oct. 30, 2020.

FIELD

The disclosure relates to a support device, more particularly to a support device for supporting a biological membrane and a method of using the same.

BACKGROUND

A bone regeneration prior to a dental implantation, for example, a guided bone regeneration (GBR), needs to use a regeneration membrane for covering a defect area so as to define the volume and type of bone that needs to be grown. The regeneration membrane has two main types: an absorbable membrane that can be absorbed by the body, and a non-absorbable membrane that cannot be absorbed by the body and that needs to be removed by a second operation. Since the material of the absorbable membrane is very soft, when a large defect area is encountered, it is often necessary to use a support structure for supporting the absorbable membrane in order to hold up the required space for bone regeneration. Generally, the method for supporting the regeneration membrane mainly includes a titanium mesh supporting method and a long bone screw supporting method.

The titanium mesh supporting method has the following drawbacks:

1. Since the titanium mesh is full of through holes, and because soft tissue grows into the through holes and adheres to the titanium mesh, it is difficult to remove the titanium mesh after the bone regeneration is completed.

2. Because the titanium mesh is full of the through holes so that the titanium mesh has an uneven and non-smooth surface, and because the titanium mesh has sharp edges between the through holes, when the titanium mesh is bent into a specific shape, a bent corner of the titanium mesh is quite rough, and it is likely that the thinner area of the gum may be pierced by the bent corner of the titanium mesh during the gum healing period after the operation, so that the bent corner of the titanium mesh is exposed from the gum, thereby leading to bone loss and tissue infection. This is the main reason for the failure of the aforesaid operation.

3. Some titanium meshes are designed to have a fixed shape and size, and are combined with a fastening member to form a support device. When the defect area is quite large, a plurality of the support devices must be simultaneously used, so that it is more complicated and inconvenient to use.

In the long bone screw supporting method, a plurality of long bone screws must first be fastened to the alveolar bone, after which the regeneration membrane is covered on the head of each long bone screw, so that the regeneration membrane is supported by the long bone screws. Because atrophy of the alveolar bone often occurs, the length of each long bone screw that can be fastened to the alveolar bone is limited. Thus, when a portion of each long bone screw that is exposed on the alveolar bone is greater than a portion thereof that fastens into the alveolar bone, each long bone screw is easily affected by an external force, causing it to shake. Further, the area of the head of each long bone screw that supports the regeneration membrane is small, so that the stability of each long bone screw to support the regeneration membrane is poor. As a result, the regeneration membrane is easy to shake, causing the bone powder that covers it to move and cannot form bone, thereby leading to failure of bone regeneration.

SUMMARY

Therefore, an object of the present disclosure is to provide a support device that can alleviate at least one of the drawbacks of the prior art.

According to one aspect of this disclosure, a support device for supporting a biological membrane includes a support bar that is elongated, that extends along a length direction and that has at least one cylindrical surface extending along the length direction for supporting the biological membrane.

Another object of the present disclosure is to provide a method of using the support device that can alleviate at least one of the drawbacks of the prior art.

According to another aspect of this disclosure, a method of using the support device, which is suitable for mounting on a space of a bone defect structure of a human body and which is suitable for supporting a biological membrane, includes the steps of: providing the support device, the support device including a support bar that is elongated, that extends along a length direction and that has at least one cylindrical surface extending along the length direction; mounting the support bar, in which the support bar is first placed in a specific position of the space of the bone defect structure, after which the support bar is fastened to the bone defect structure; and covering with the biological membrane, in which the biological membrane is covered on the bone defect structure to conceal the space and the support bar, the support bar supporting the biological membrane through the at least one cylindrical surface.

BRIEF DESCRIPTION OF THE DRAWINGS

Other features and advantages of the disclosure will become apparent in the following detailed description of the embodiments with reference to the accompanying drawings, of which.

DETAILED DESCRIPTION

Figure 1:
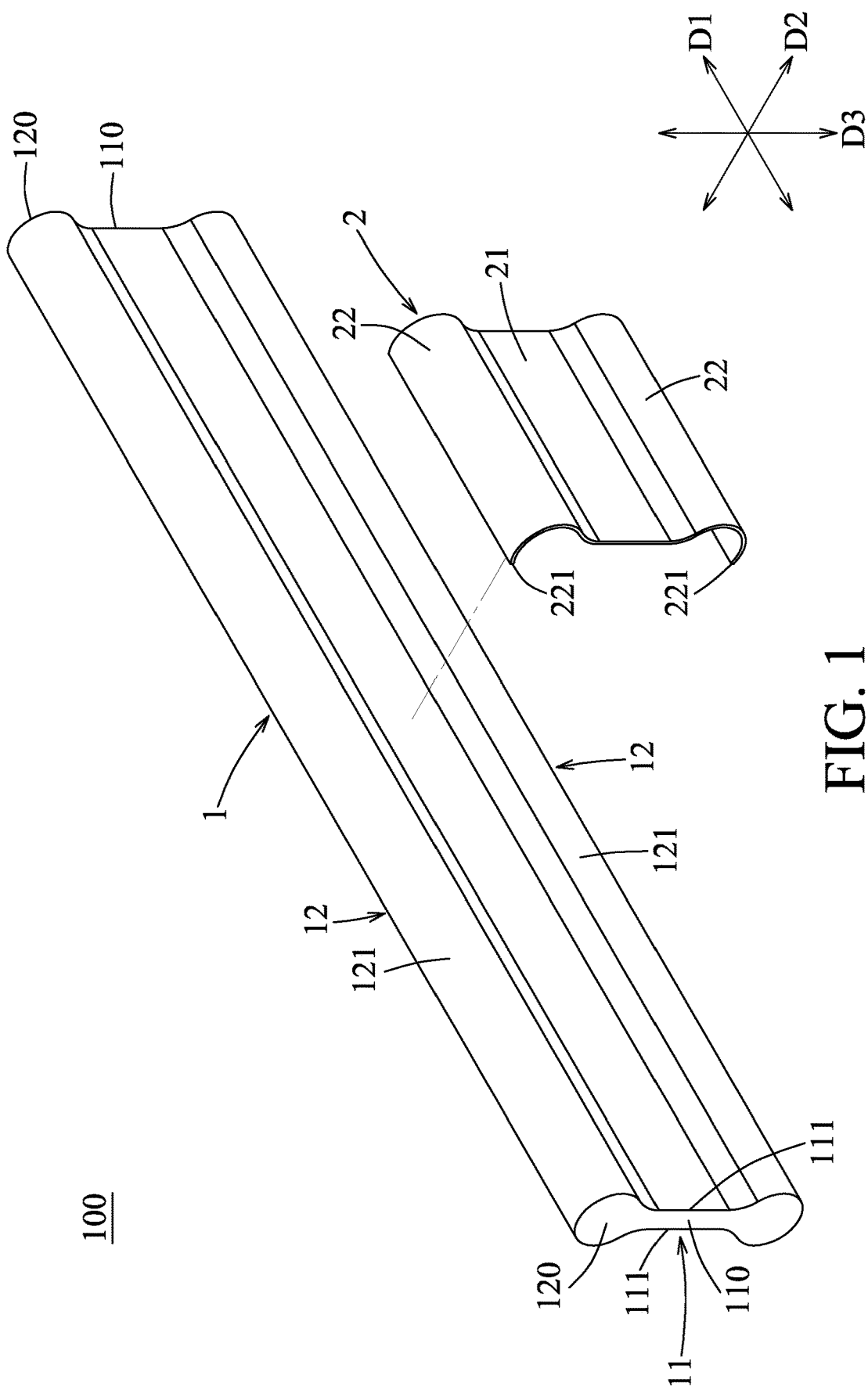
FIG. 1 is an exploded perspective view of a support device according to the first embodiment of the present disclosure.

Before the present disclosure is described in greater detail with reference to the accompanying embodiments, it should be noted herein that like elements are denoted by the same reference numerals throughout the disclosure.

Figure 2:
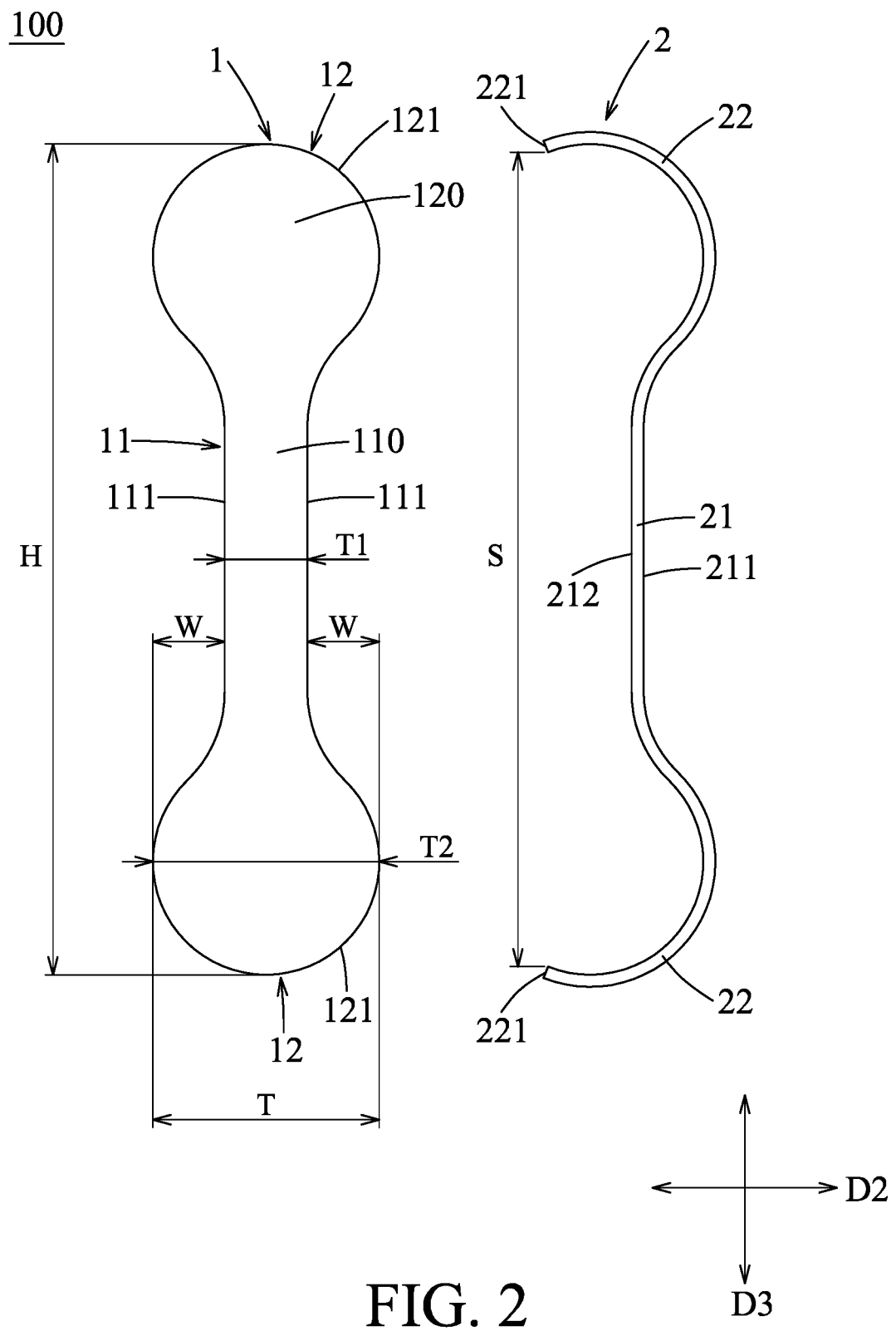
FIG. 2 is a side view of a support bar and a clamping plate of the first embodiment.

Referring to FIGS. 1 and 2, a support device 100 according to the first embodiment of the present disclosure is shown to include a support bar 1 and a clamping plate 2.

The support bar 1 is made by, for example, a casting method or a CNC machining method, and the material thereof is exemplified as titanium. The support bar 1 is elongated, extends along a length direction (D1), and includes a middle portion 11 and two end portions 12. The middle portion 11 has a plate shape extending along the length direction (D1), and has two end faces 110 opposite to each other along the length direction (D1), and two side surfaces 111 connected between the end faces 110 and opposite to each other along a thickness direction (D2) transverse to the length direction (D1). The end portions 12 are formed on two ends of the middle portion 11 that are opposite to each other along a height direction (D3) transverse to the length direction (D1) and the thickness direction (D2). Each end portion 12 is cylindrical, and has a cylindrical surface 121 extending along the length direction (D1), and two end faces 120 respectively connected to two opposite ends of the cylindrical surface 121 of a corresponding one of the end portions 12. Each end face 110 of the middle portion 11 is connected between one of the end faces 120 of one of the end portions 12 and a corresponding one of the end faces 120 of the other end portion 12. The cylindrical surface 121 of each end portion 12 is connected to and protrudes out of the side surfaces 111 of the middle portion 11 for supporting, for example, a biological membrane 4 (see FIG. 6) that serves as a regeneration membrane.

The support bar 1 has a height (H) extending in the height direction (D3) smaller than or equal to 3 mm, and a largest thickness (T) extending in the thickness direction (D2) greater than or equal to 1 mm. In this embodiment, the height (H) is 3 mm, and the largest thickness (T) is 1 mm. Because the thickness of the support bar 1 is very thin, it is flexible. Specifically, because the cylindrical surface 121 of each end portion 12 protrudes from the side surfaces 111 of the middle portion 11, the middle portion 11 has a first thickness (T1) extending in the thickness direction (D2) smaller than a second thickness (T2) of each end portion 12 extending in the thickness direction (D2). In this embodiment, the first thickness (T1) is 0.5 mm, while the second thickness (T2) is 1 mm and is similar to the largest thickness (T). The cylindrical surface 121 of each end portion 12 protrudes from a corresponding one of the side surfaces 111 by a distance (W) of 0.25 mm. Through this, the support bar 1 can be easily bent and deformed into a desired specific shape, and can maintain sufficient support strength at the same time.

The material of the clamping plate 2 is exemplified as titanium. The clamping plate 2 is detachably clamped to the support bar 1 for fixing the biological membrane 4 to the support bar 1, and includes a main plate body 21 and two elastic plate bodies 22. The main plate body 21 matches the shape of a corresponding one of the side surfaces 111 of the middle portion 11, and is used for pressing the biological membrane 4. The main plate body 21 has an outer side surface 211 and an inner side surface 212. The elastic plate bodies 22 are respectively bent from two opposite ends of the main plate body 21, and are spaced apart from each other along the height direction (D3). The elastic plate bodies 22 are used for clamping the biological membrane 4 and the cylindrical surfaces 121 of the end portions 12. Each elastic plate body 22 first extends outwardly and curvedly from one end of the main plate body 21 for a certain distance away from the outer side surface 211, and then extends inwardly and curvedly for a certain distance away from the inner side surface 212, so that each elastic plate body 22 forms an arc structure with a shape matching that of the cylindrical surface 121 of the respective end portion 12. Each elastic plate body 22 is used for pressing the biological membrane 4 against the cylindrical surface 121 of the respective end portion 12, and has a free end 221. The free ends 221 of the elastic plate bodies 22 are spaced apart from each other by a distance (S) which is smaller than the height (H). Through this, when each elastic plate body 22 is mounted on the respective end portion 12, the free end 221 thereof can slide on the cylindrical surface 121 of the respective end portion 12 to urge each elastic plate body 22 to bend and deform relative to the main plate body 21, so that each elastic plate body 22 can be engaged to the respective end portion 12.

Below is a detailed description of a method of using the support device 100 of the first embodiment.

Figure 3:
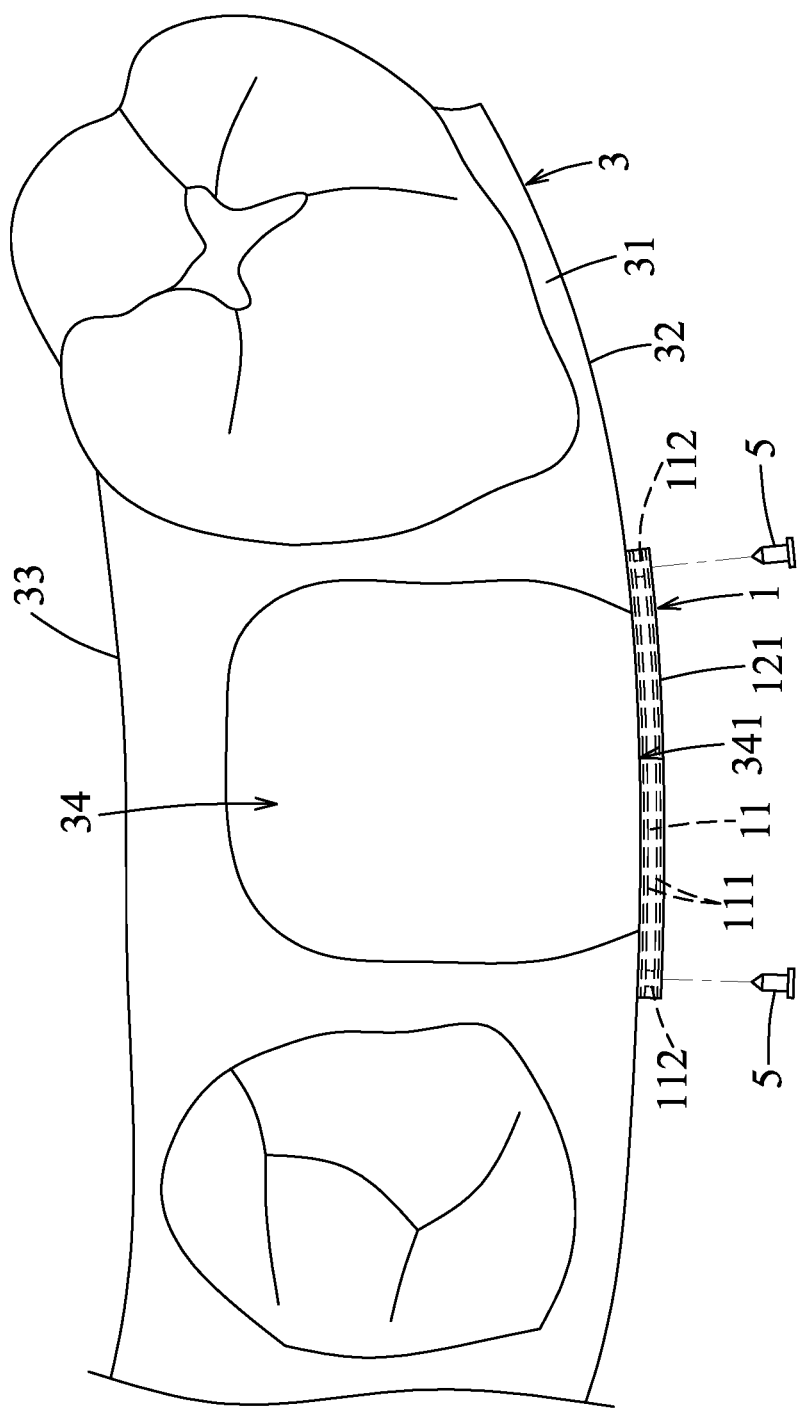
FIG. 3 is a fragmentary top view, illustrating the first embodiment being applied to a bone defect structure.
Figure 6:
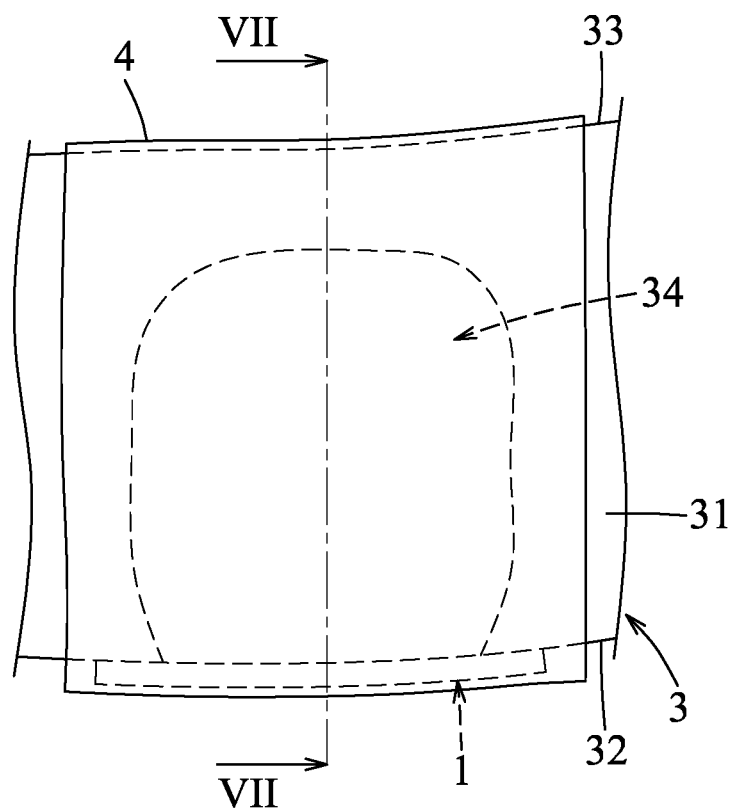
FIG. 6 is another fragmentary top view, illustrating the first embodiment being applied to the bone defect structure.

Referring to FIG. 3, the support device 100 (see FIG. 1) is suitable to be mounted on a bone defect structure 3 of a human body, and is used for supporting the biological membrane 4 (see FIG. 6). The bone defect structure 3 is an alveolar bone as an example, and has a top end 31, a buccal side 32, a lingual side 33, and a space 34 defined by the top end 31 and a portion of the buccal side 32. The space 34 has a corner portion 341 between the top end 31 and the buccal side 32.

Figure 4:
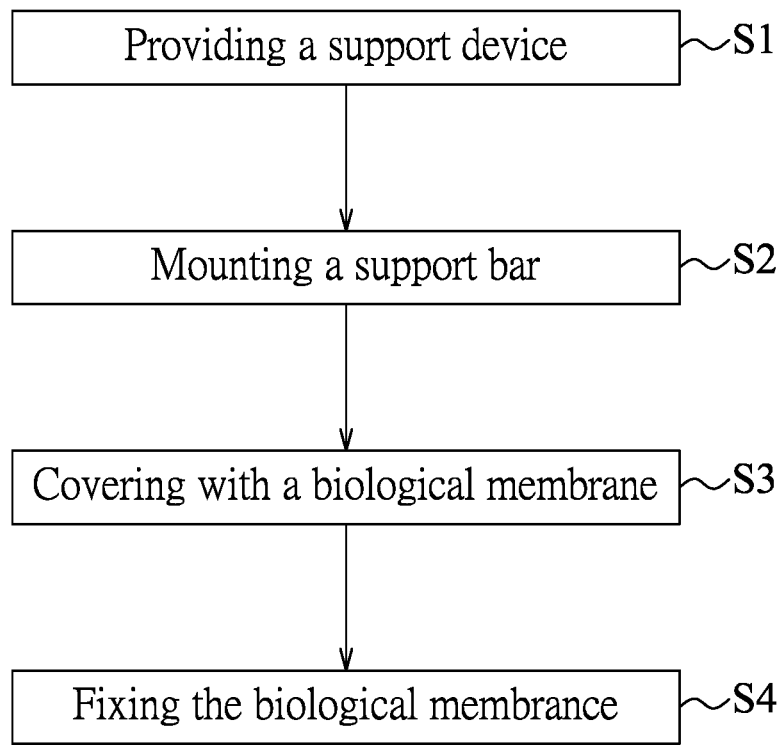
FIG. 4 is a flow chart, illustrating the steps involved in a method of using the first embodiment.

FIG. 4 is a flow chart that illustrates the steps involved in the method of using the support device 100 of the first embodiment. The method of using the support device 100 includes the steps of: providing the support device 100 (step S1), mounting the support bar 1 (step S2), covering with the biological membrane 4 (step S3), and fixing the biological membrane 4 (step S4).

In the step of providing the support device 100 (step S1), with reference to FIGS. 1 and 4, the support device 100 includes the support bar 1 and the clamping plate 2.

Figure 5:
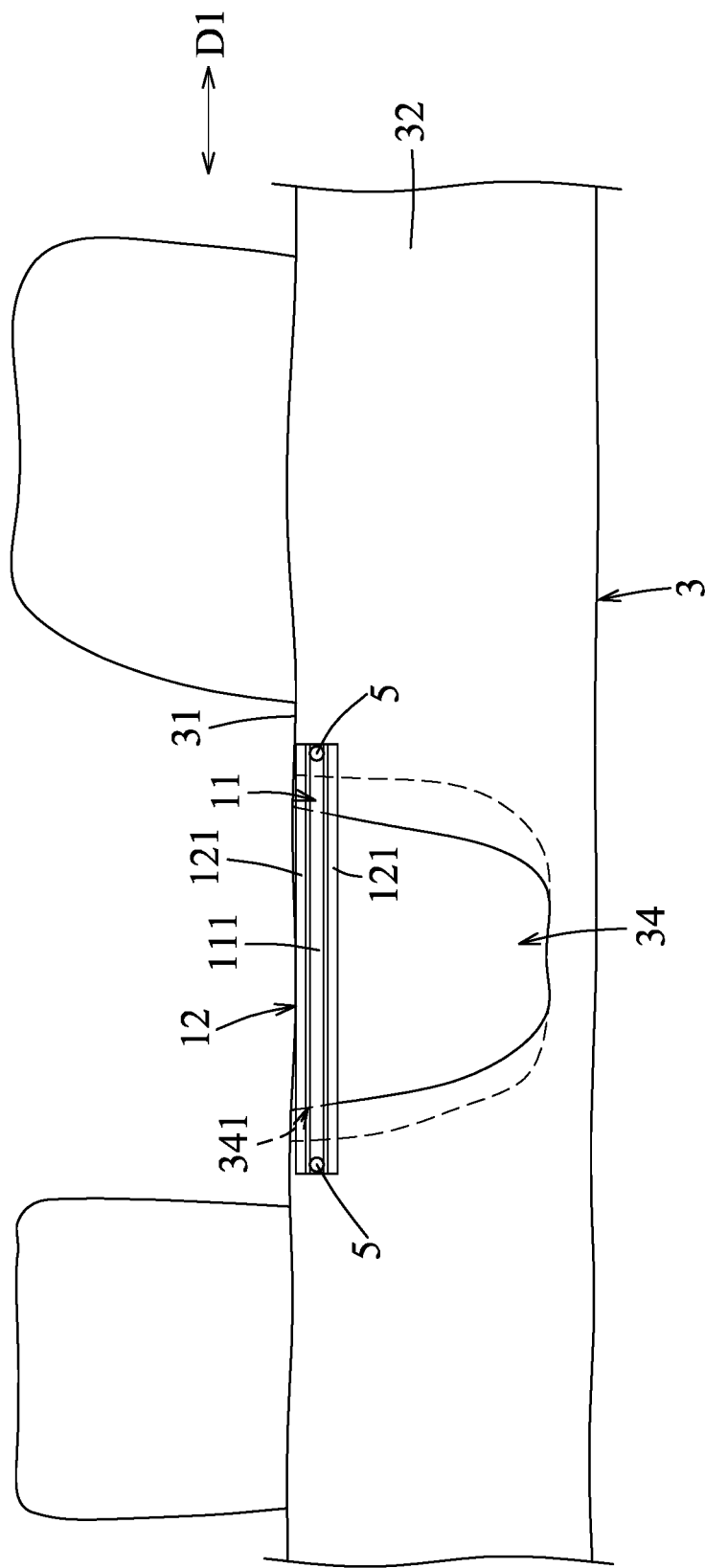
FIG. 5 is a fragmentary side view, illustrating the first embodiment being applied to the bone defect structure.

In the step of mounting the support bar 1 (step S2), with reference to FIGS. 3 to 5, firstly, a tool, such as pliers, is needed to make two through holes 112 in an appropriate position of the middle portion 11 of the support bar 1. Each through hole 112 extends between the side surfaces 111 of the middle portion 11. The through holes 112 are spaced apart from each other along the length direction (D1) and are respectively proximate to the end faces 110 (see FIG. 1) of the middle portion 11.

Afterwards, the support bar 1 is placed in a specific position of the space 34 of the bone defect structure 3. In this embodiment, the specific position refers to a position corresponding to the corner portion 341 of the space 34. For example, the cylindrical surfaces 121 of the end portions 12 of the support bar 1 are placed to abut against the buccal side 32 in proximity to the top end 31, so that the support bar 1 corresponds to and spans across the corner portion 341 of the space 34. Subsequently, two bone screws 5 are respectively inserted through the through holes 112 and are screwed to the buccal side 32 so as to fix the support bar 1 to the buccal side 32 of the bone defect structure 3. It should be noted that the following two methods for mounting the support bar 1 may also be adopted according to the requirement: (1) the cylindrical surfaces 121 of the end portions 12 of the support bar 1 may first be placed to abut against the top end 31 in proximity to the buccal side 32, after which two bone screws 5 are used to fix the support bar 1 to the top end 31 of the bone defect structure 3; and (2) the cylindrical surfaces 121 of the end portions 12 of the support bar 1 may first be placed to abut against a junction of the top end 31 and the buccal side 32, after which two bone screws 5 are used to fix the support bar 1 to the junction of the top end 31 and the buccal side 32 of the bone defect structure 3. Through this, the support bar 1 may similarly correspond to and span across the corner portion 341 of the space 34.

Through the configuration of the support bar 1, that is, with the two end portions 12 formed on the two opposite ends of the middle portion 11 thereof, the support bar 1 can be fastened to the bone defect structure 3 either in an angular position, as shown in FIG. 5, or in an angular position rotated 180 degrees around the centerline of the middle portion 11 which extends along the length direction (D1). Through this, the convenience of assembly can be improved.

Figure 7:
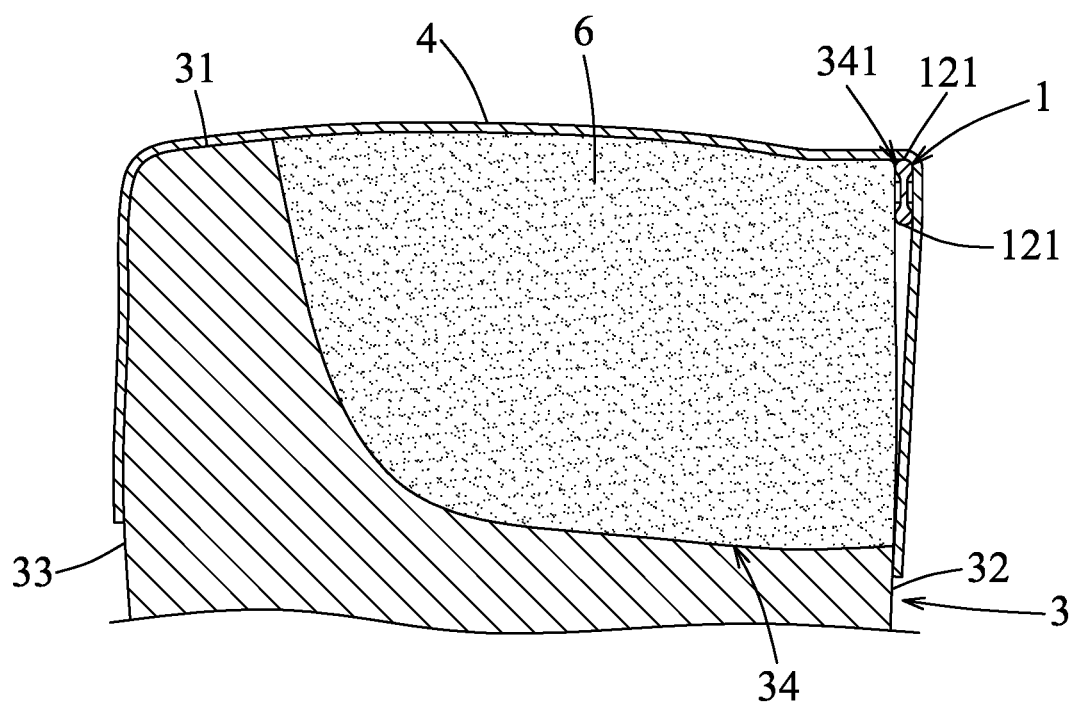
FIG. 7 is a sectional view taken along line VII-VII of FIG. 6.

In the step of covering with the biological membrane 4 (step S3), with reference to FIGS. 4, 6 and 7, firstly, a portion of the biological membrane 4 is placed to cover the lingual side 33 of the bone defect structure 3, and is fixed thereto by stitching (not shown). Next, bone powder 6 is filled into the space 34, after which the top end 31, the space 34, the support bar 1 and the buccal side 32 are covered by the remaining portion of the biological membrane 4, so that the biological membrane 4 hides the space 34 and the support bar 1. At this time, the support bar 1 supports the biological membrane 4 through the cylindrical surfaces 121 thereof.

In the step of fixing the biological membrane 4 (step S4), with reference to FIGS. 2, 4, 8 and 9, a lateral force (F) is applied to the clamping plate 2 so as to move it laterally toward the support bar 1. Since the distance (S) between the free ends 221 of the elastic plate bodies 22 is smaller than the height (H), during the lateral movement of the clamping plate 2 toward the support bar 1, the free ends 221 of the elastic plate bodies 22 will contact and press the biological membrane 4 against the cylindrical surfaces 121 of the end portions 12 of the support bar 1. Subsequently, the free ends 221 of the elastic plate bodies 22 will slide along the cylindrical surfaces 121 of the respective end portions 12 to urge the elastic plate bodies 22 to bend and deform relative to the main plate body 21 for storing restoring forces. Since a portion of each elastic plate body 22 protrudes out of the outer side surface 211 of the main plate body 21, when each elastic plate body 22 is bent and deformed relative to the main plate body 21, it will drive the main plate body 21 to slightly deform inward. When the free end 221 of each elastic plate body 22 slides over the cylindrical surface 121 of the respective end portion 12, each elastic plate body 22 will automatically engage with the respective end portion 12 through the restoring force thereof. Through this, the elastic plate bodies can clamp the biological membrane 4 and the cylindrical surfaces 121 of the end portions 12 to thereby fix the biological membrane 4 to the support bar 1. Because of the slight inward deformation of the main plate body 21, the inner side surface 212 of the main plate body 21 can push a portion of the biological membrane 4 to tightly abut against a corresponding side surface 111 of the middle portion 11. With the shape of each elastic plate body 22 matching with the corresponding cylindrical surface 121, each elastic plate body 22 can push a portion of the biological membrane 4 to tightly abut against the corresponding cylindrical surface 121. Through this, the support bar 1and the clamping plate 2 can have a large contact area with the biological membrane 4 to improve the stability of fixing the biological membrane 4.

Through the configuration of the cylindrical surface 121 of each end portion 12 protruding out of the side surfaces 111 of the middle portion 11, when the support bar 1 faces the buccal side 32 with any one of the side surfaces 111 thereof and is fastened to the buccal side 32, the free end 221 of each elastic plate body 22 can press the biological membrane 4 against the cylindrical surface 121 of the respective end portion 12 and can slide along the cylindrical surface 121, so that each elastic plate body 22 can smoothly engage with the respective end portion 12. Through this, the clamping plate 2 will not be affected by the assembling direction of the support bar 1, so that the convenience of assembly of the clamping plate 2 can be improved.

It should be noted that in other implementations of the first embodiment, each elastic plate body 22 may not protrude out of the outer side surface 212 of the main plate body 21, rather it may extend inwardly and curvedly from one end of the main plate body 21, so that after the clamping plate 2 fixes the biological membrane 4 to the support bar 1, the biological membrane 4 is spaced apart from the corresponding side surface 111 by a distance.

After the clamping plate 2 fixes the biological membrane 4 to the support bar 1, a skin flap (not shown) is used to completely cover the biological membrane 4 and the support device 100, and is sewn thereto. Through this, after the gum is healed, it can completely cover the biological membrane 4 and the support device 100.

Figure 8:
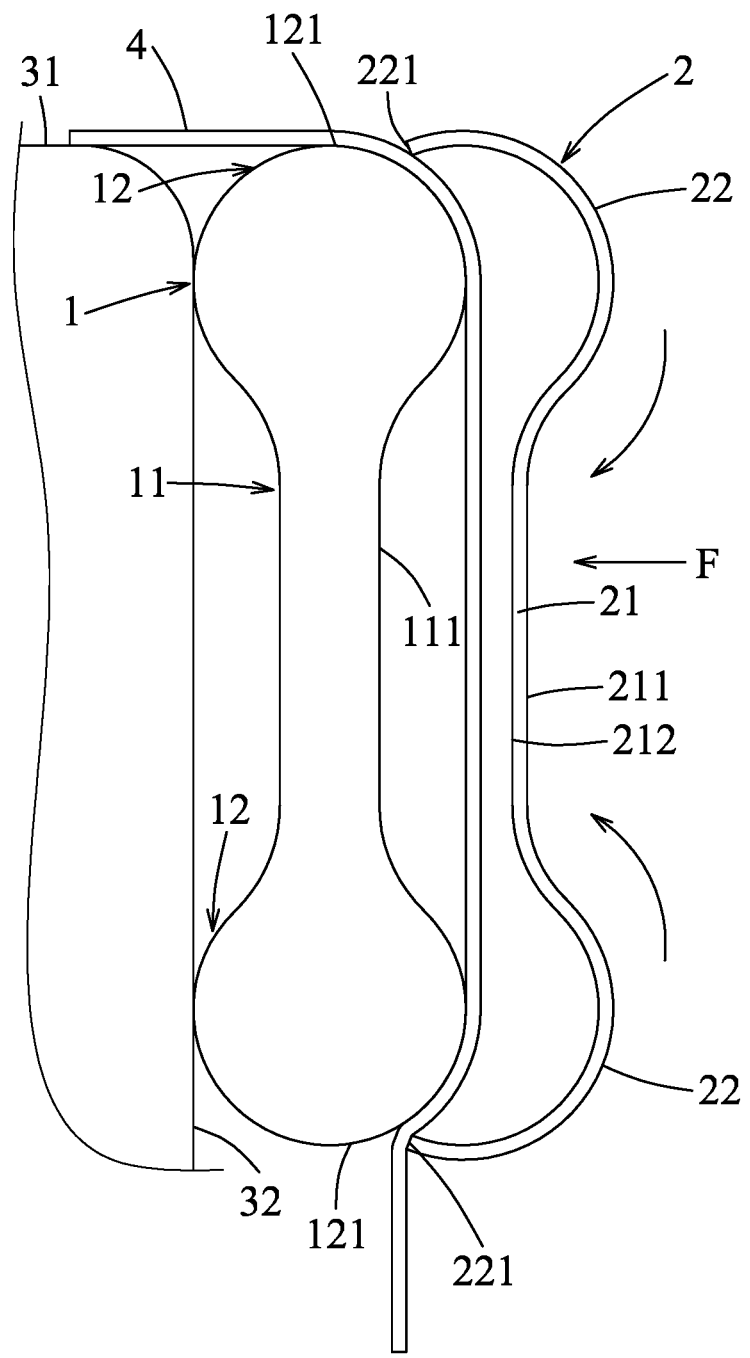
FIG. 8 illustrates how the clamping plate of the first embodiment is assembled to the support bar.
Figure 9:
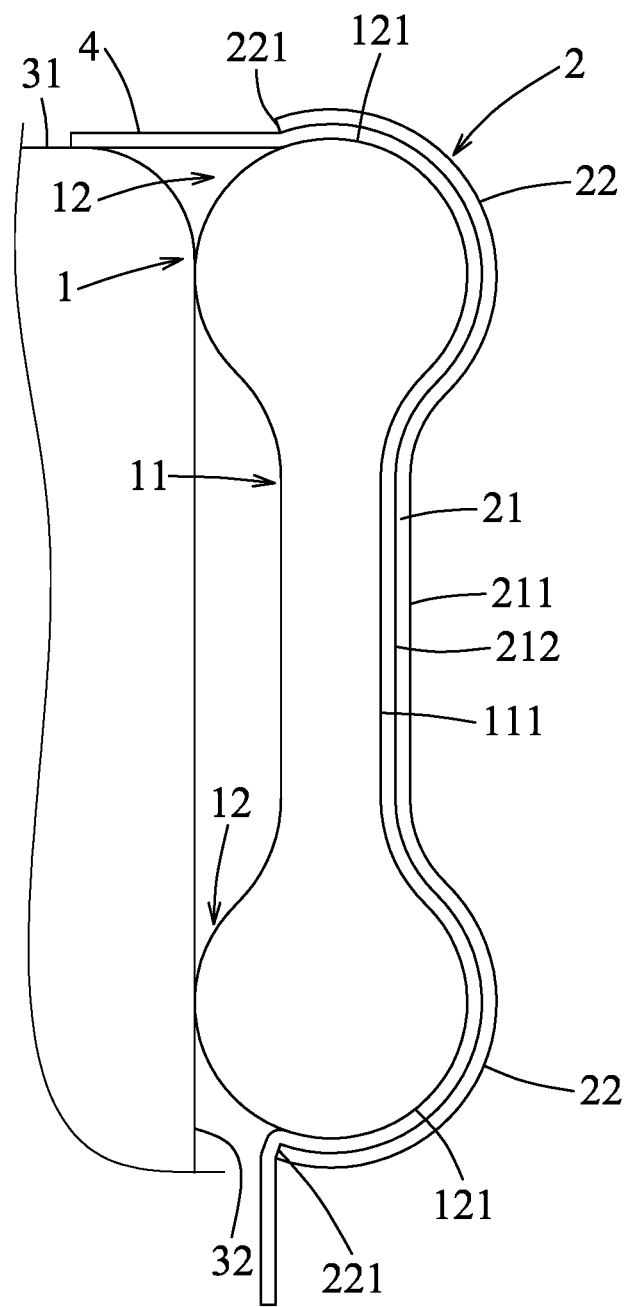
FIG. 9 illustrates how the clamping plate fixedly clamp a biological membrane to the support bar.

With reference to FIGS. 2, 8 and 9, in this embodiment, the support bar 1 uses the smooth cylindrical surfaces 121 of the end portions 12 to support the biological membrane 4, so that the gum can be prevented from being pierced by any of the end portions 12 during the healing period thereof, and so that the support bar 1 can be prevented from being exposed from the bone grafting area which may cause failure of the operation. Further, since the middle portion 11 of the support bar 1 is only formed with the through holes 112 (see FIG. 3) for extension of the bone screws 5 (see FIG. 5) therethrough and no other holes, soft tissue can be prevented from growing and adhering to the support bar 1 during the healing period of the gum. Through this, after the gum is healed, a slot is cut on the gum, the clamping plate 2 is first detached from the support bar 1, after which the bone screws 5 are unscrewed, and the support bar 1 can then be conveniently and quickly removed from the gum. On the other hand, through the configuration of the clamping plate 2, the clamping plate 2 can fix the biological membrane 4 to the support bar 1 conveniently and quickly and can prevent the biological membrane 4 from shaking relative to the support bar 1. Moreover, since the support bar 1 is elongated and can span across the corner portion 341 of the space 34 (see FIG. 3), a single set of the support device 100 can be used to achieve the effect of stably supporting the biological membrane 4. Thus, the convenience of assembly and disassembly of the support device 100 can be enhanced.

The support bar 1 of the support device 100 of this embodiment can have the following different aspects depending on the requirements:

1. The cylindrical surfaces 121 of the end portions 12 may be configured to only protrude out of one of the side surfaces 111 of the middle portion 11, and the one of the side surfaces 111 may face the clamping plate 2 during assembly and use of the support bar 1.

2. The number of the end portion 12 of the support bar 1 may be one, and the cylindrical surface 121 of the end portion 12 may be configured to simultaneously protrude out of the side surfaces 111 of the middle portion 11. The end portion 12 may face upward during assembly and use of the support bar 1.

3. The number of the end portion 12 of the support bar 1 may be one, and the cylindrical surface 121 of the end portion 12 may be configured to only protrude out of one of the side surfaces 111 of the middle portion 11. The end portion 12 may face upward when the support bar 1 is assembled and used, and the one of the side surfaces 111 may face the clamping plate 2 during assembly and use of the support bar 1.

Specifically, in another implementation of this embodiment, the support device 100 may only include the support bar 1. In the step of fixing the biological membrane 4 (step S4) of this case, the biological membrane 4 may be fixed to the buccal side 32 by stitching (not shown). The effect of fixing the biological membrane 4 can be similarly achieved.

Figure 10:
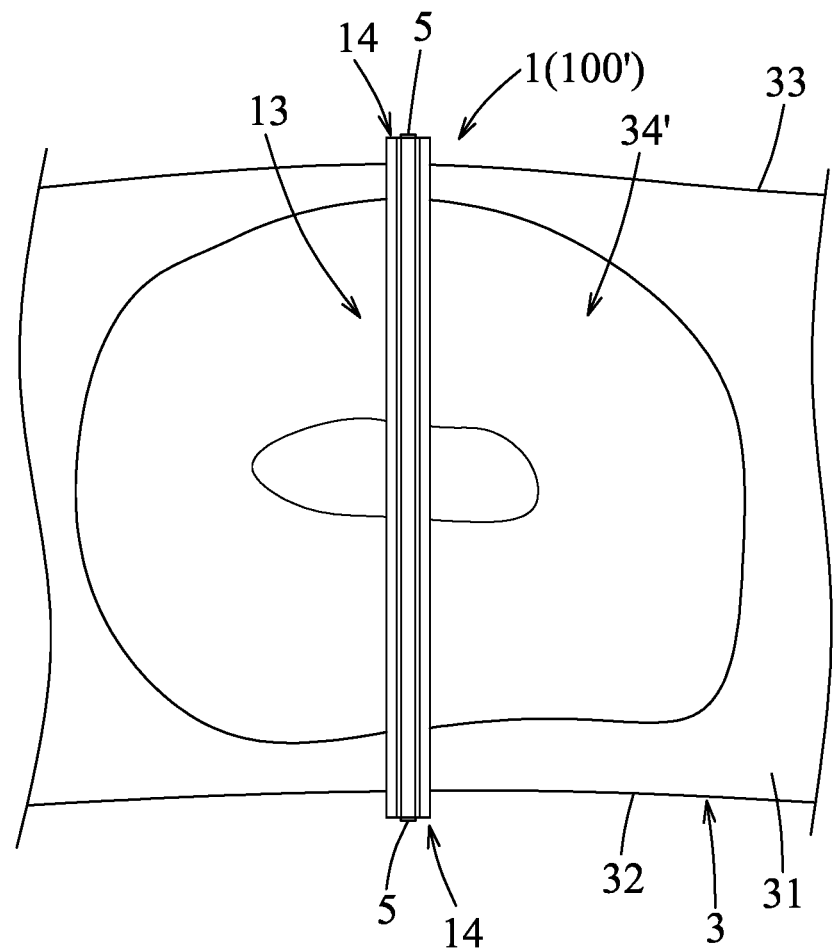
FIG. 10 is a fragmentary top view, illustrating a support device according to the second embodiment of the present disclosure being applied to the bone defect structure.
Figure 11:
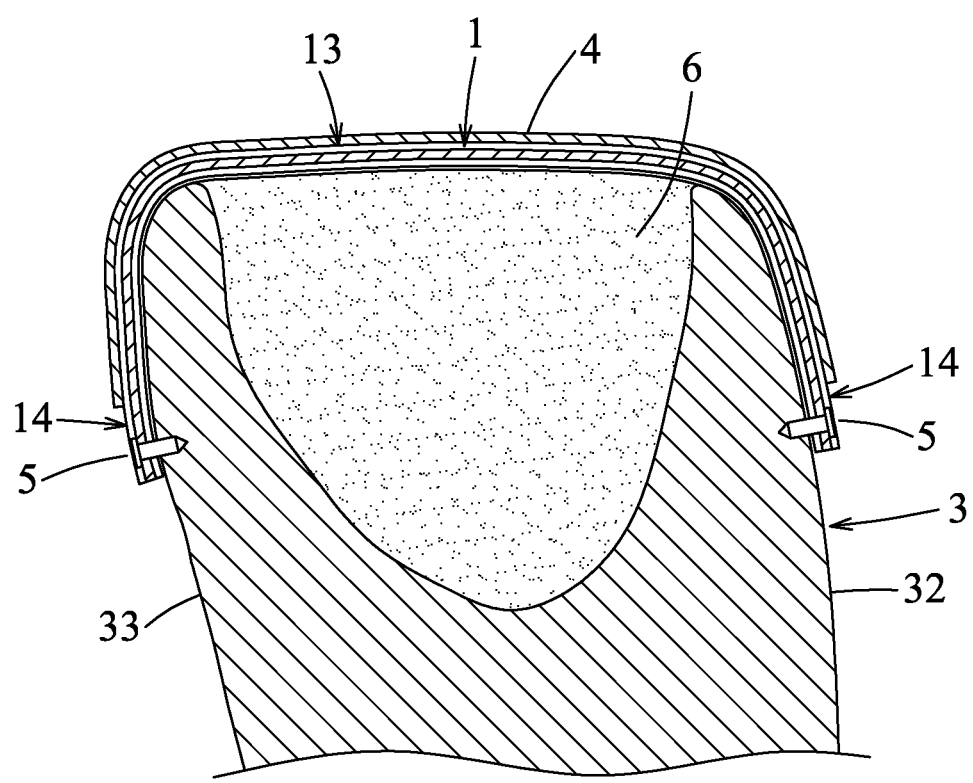
FIG. 11 is a fragmentary sectional view, illustrating the second embodiment being applied to the bone defect structure.

Referring to FIGS. 10 and 11, the second embodiment of the support device 100' of this disclosure is shown to be identical to the first embodiment in structure, but differs in the method of using the support device 100'. In the second embodiment, the space 34' of the bone defect structure 3 extends inwardly from the top end 31 thereof. In the step of mounting the support bar 1 (step S2) (see FIG. 4), the support bar 1 is first bent to form an inverted U-shape so that the support bar 1 is formed with a top support portion 13 and two side support portions 14 located on two opposite ends of the top support portion 13, after which the support bar 1 is mounted on the bone defect structure 3 with the top support portion 13 disposed on top of and spanning across the space 34' and the side support portions 14 respectively abutting against the buccal side 32 and the lingual side 33. Subsequently, the side support portions 14 are respectively fixed to the buccal side 32 and the lingual side 33 by using two bone screws 5, thereby fixing the support bar 1 to the bone defect structure 3. Afterwards, the biological membrane 4 is placed to cover the support bar 1, the buccal side 32 and the lingual side 33, and the clamping plate 2 (see FIG. 9) fixes the biological membrane 4 to the top support portion 13 of the support bar 1.

Since the side support portions 14 of the support bar 1 are respectively fixed to the buccal side 32 and the lingual side 33 by the bone screws 5, the support bar 1 can be stably fixed to the bone defect structure 3 and is not easy to shake. Further, with the support bar 1 being bent to form into the inverted U-shape, the support bar 1 can use the top support portion 13 and the side support portions 14 thereof to simultaneously support the biological membrane 4. Since the area of the support bar 1 supporting the biological membrane 4 is large, the support bar 1 can achieve the effect of stably supporting the biological membrane 4. In comparison with the long bone screw support method in the prior art, the present disclosure can more accurately control the shape of the bone powder 6 after it has grown into bone.

Figure 12:
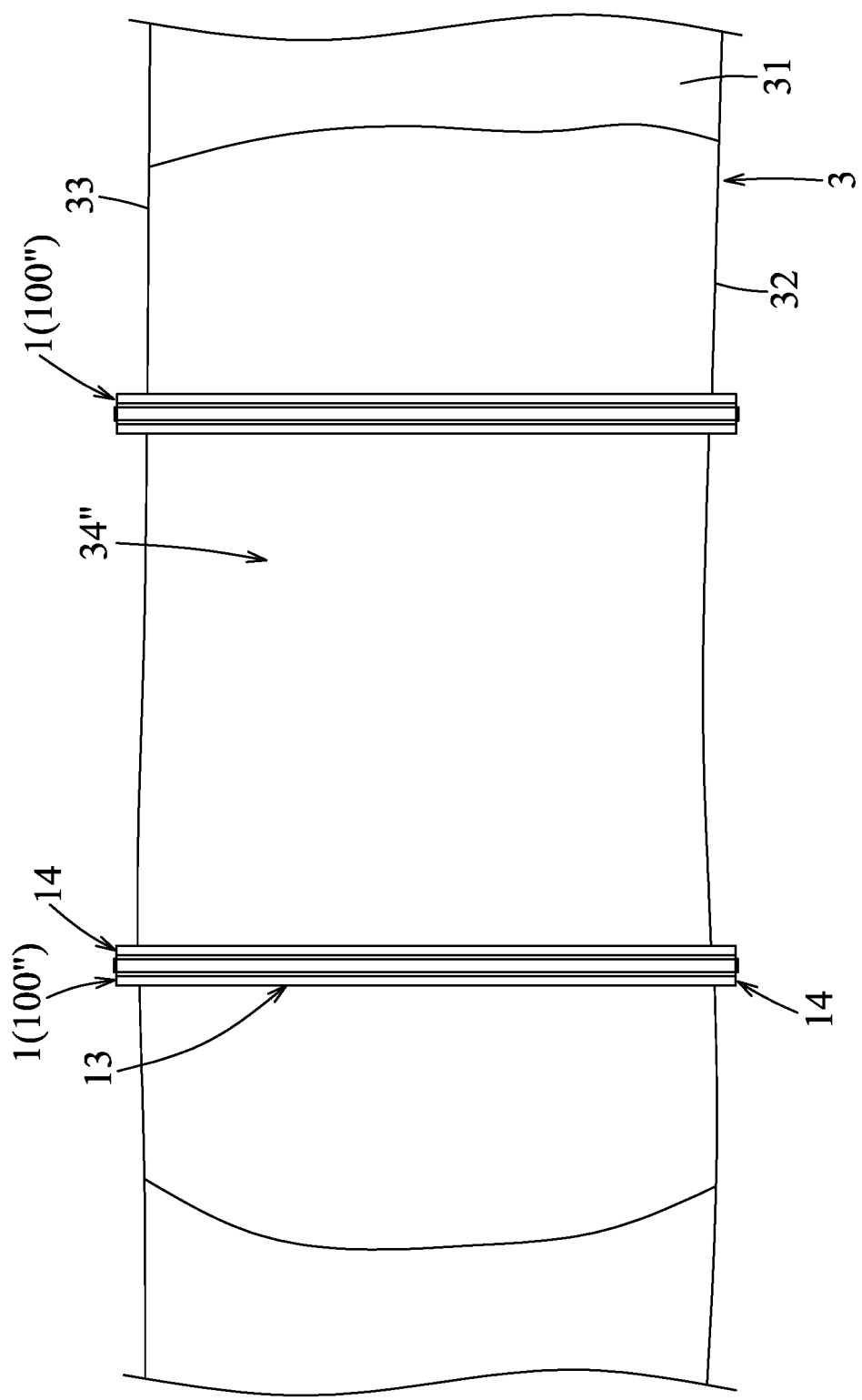
FIG. 12 is a fragmentary top view, illustrating a support device according to the third embodiment of the present disclosure being applied to the bone defect structure.
Figure 13:
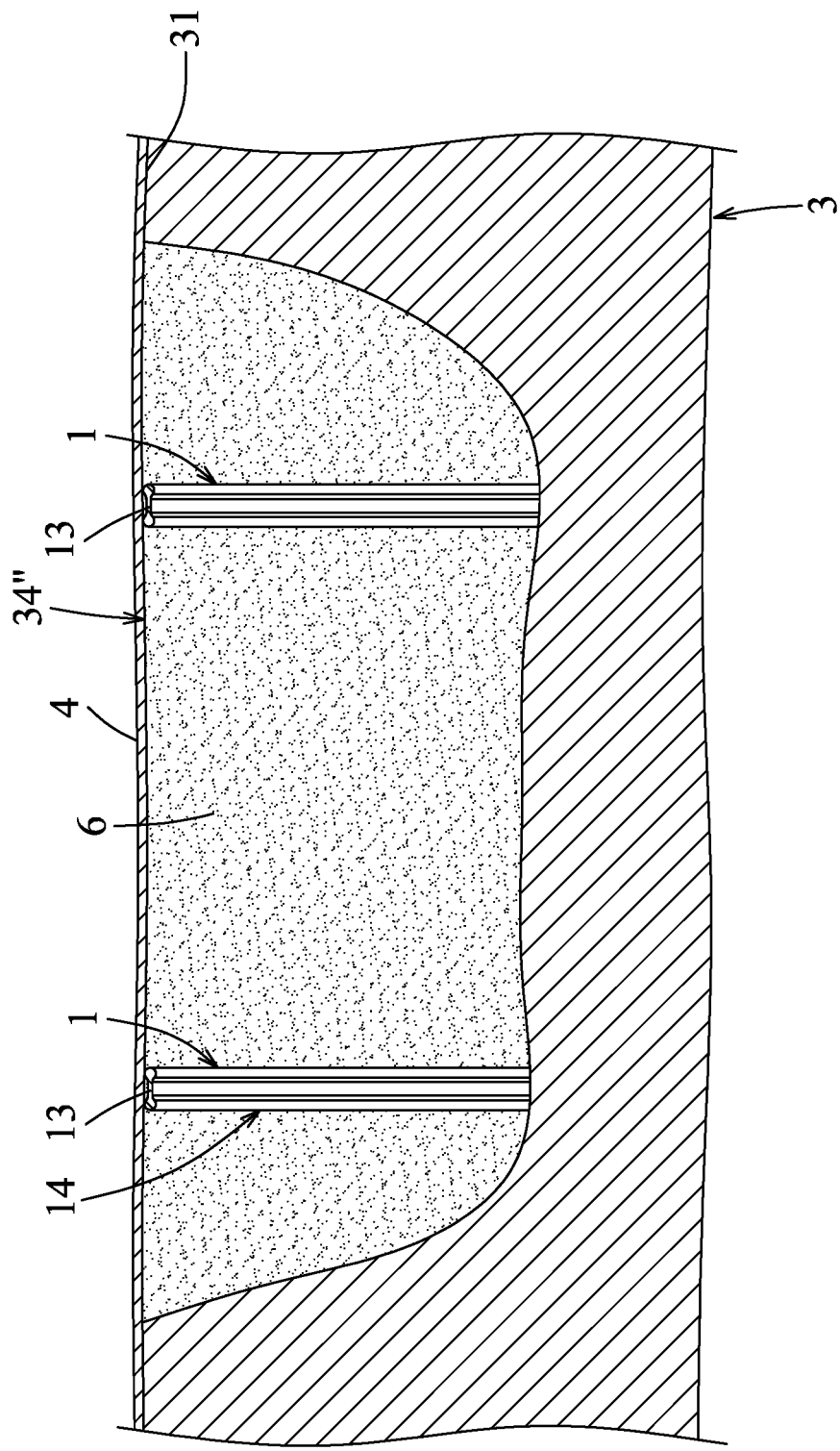
FIG. 13 is a fragmentary sectional view, illustrating the third embodiment being applied to the bone defect structure.

Referring to FIGS. 12 and 13, the third embodiment of the support device 100" of this disclosure is shown to be identical to the second embodiment in structure and the method of use, and only differs in the number of the support device 100". In the third embodiment, the space 34" of the bone defect structure 3 extends inwardly from the top end 31 thereof, is located between the buccal side 32 and the lingual side 33, and covers a large area. In the step of providing the support device 100" (step S1) (see FIG. 4), the number of the support device 100" of this embodiment is multiple, and the number of using the support device 100" depends upon the size of area covered by the space 34". In the step of mounting the support bar 1 (step S2) (see FIG. 4), the support bar 1 of each support device 100" is first bent to form an inverted U-shape, and the support bars 1 of the support devices 100" are arranged spaced apart from each other on the bone defect structure 3. Subsequently, the support bars 1 are fastened to the bone defect structure 3. Since the side support portions 14 of each support bar 1 are respectively fixed to the buccal side 32 and the lingual side 33 through the bone screws 5 (see FIG. 11), each support bar 1 can be stably fixed to the bone defect structure 3 and is not easy to shake. Further, with each support bar 1 being bent to form the inverted U-shape and with the support bars 1 simultaneously supporting the biological membrane 4, the effect of stably supporting the biological membrane 4 can be achieved. In comparison with the long bone screw support method in the prior art, the present disclosure can more accurately control the shape of the bone powder 6 after it has grown into bone.

Figure 14:
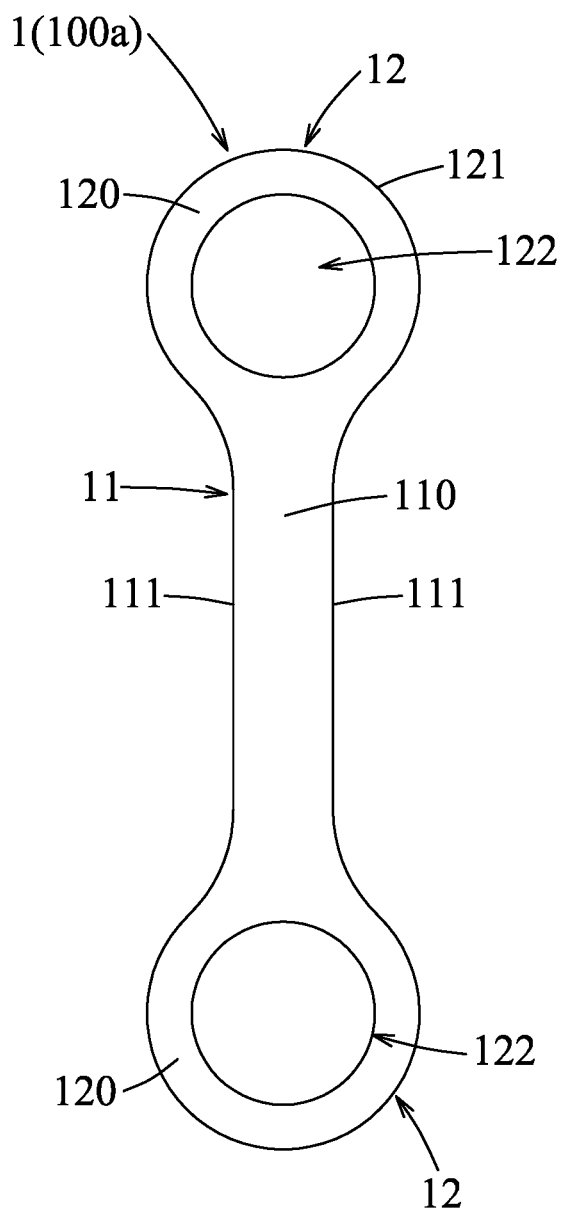
FIG. 14 is a side view of a support bar of a support device according to the fourth embodiment of the present disclosure.

Referring to FIG. 14, the fourth embodiment of the support device (100*a*) of this disclosure is shown to be identical to the first embodiment, and only differs in the structure of the support bar 1. In the fourth embodiment, each end portion 12 of the support bar 1 is formed with a through passage 122 extending between the end faces 120 along the length direction (D1) (see FIG. 1). Through this, each end portion 12 can be clamped and flattened using an auxiliary tool, so that each end portion 12 can abut against a surface of the bone defect structure 3 (see FIG. 3) with large undulation.

Figure 15:
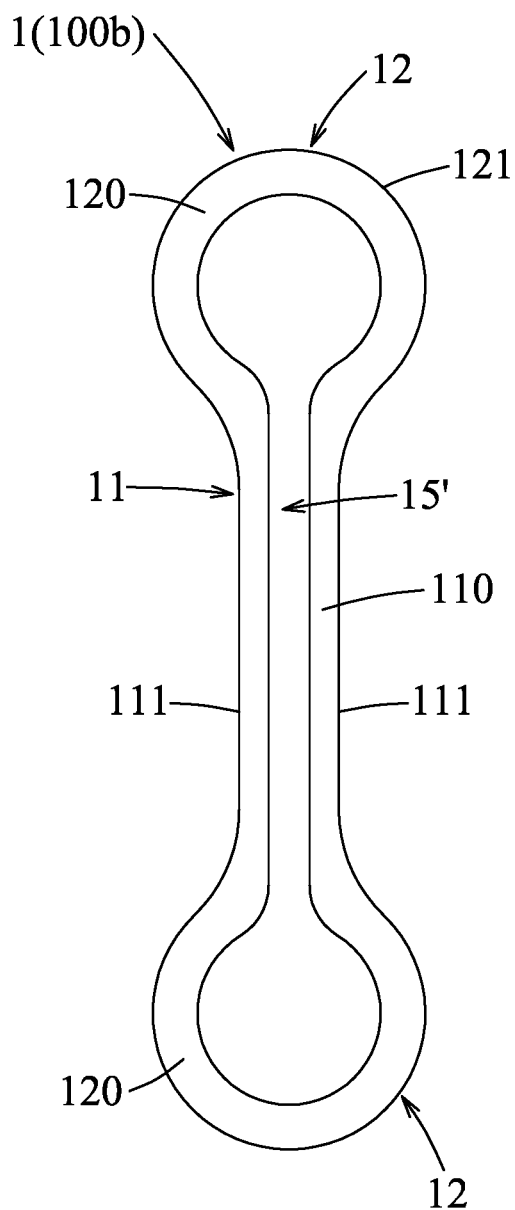
FIG. 15 is a side view of a support bar of a support device according to the fifth embodiment of the present disclosure.

Referring to FIG. 15, the fifth embodiment of the support device (100*b*) of this disclosure is shown to be identical to the first embodiment, and only differs in the structure of the support bar 1. In the fifth embodiment, the middle portion 11 and the end portions 12 of the support bar 1 cooperatively define a through passage 15' that extends between the end faces 110 of the middle portion 11 and between the end faces 120 of each end portion 12 along the length direction (D1) (see FIG. 1). Through this, the middle portion 11 and the end portions 12 can be clamped and flattened using an auxiliary tool, so that the support bar 1 can abut against a surface of the bone defect structure 3 (see FIG. 3) with large undulation.

Figure 16:
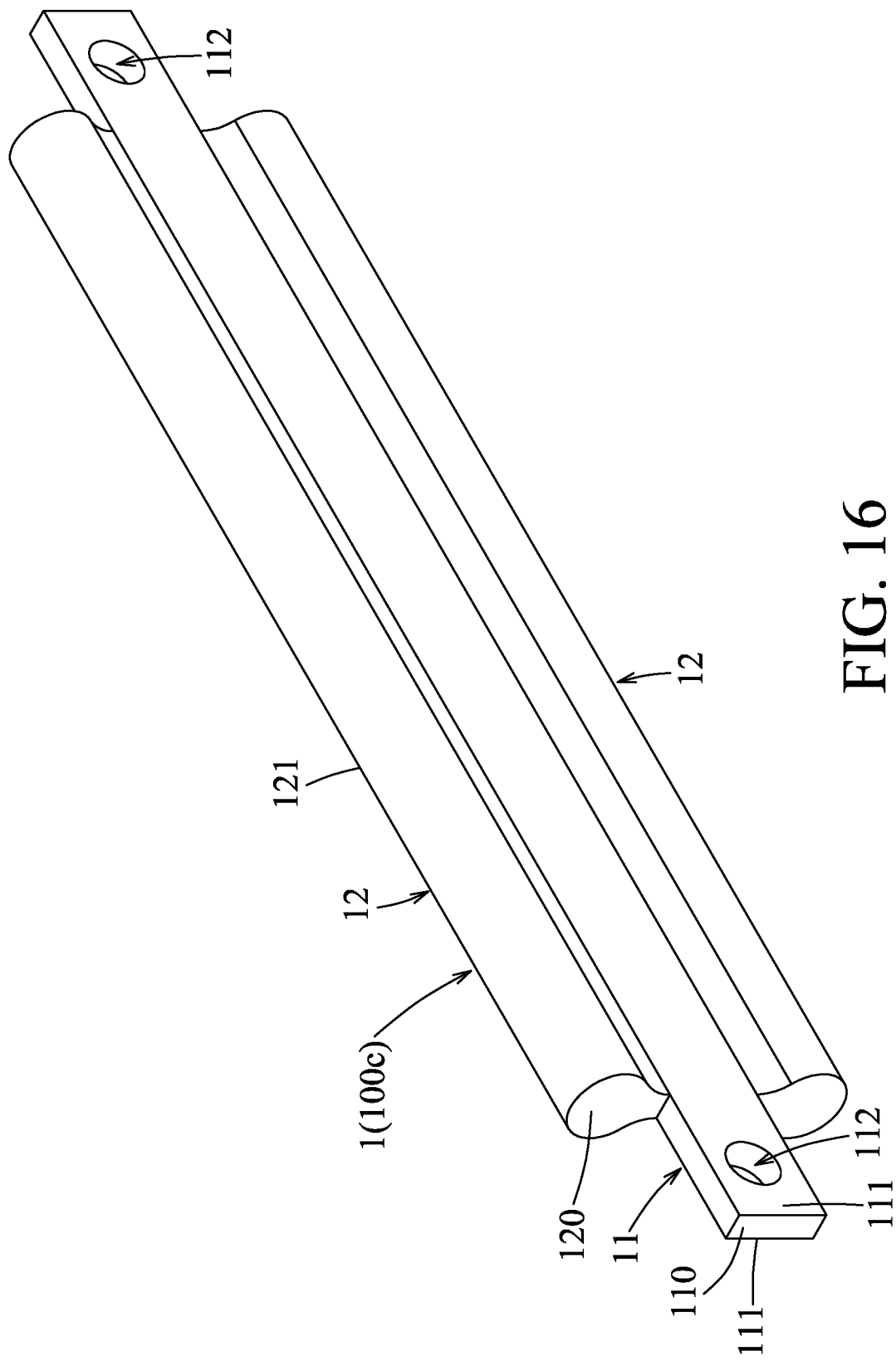
FIG. 16 is a side view of a support bar of a support device according to the sixth embodiment of the present disclosure.

Referring to FIG. 16, the sixth embodiment of the support device (100*c*) of this disclosure is shown to be identical to the first embodiment, and only differs in the structure of the support bar 1. In the sixth embodiment, two opposite ends of each end portion 12 of the support bar 1 are cut to appropriate lengths using a cutting tool such that each end face 110 of the middle portion 11 protrudes out of the end face 120 of each end portion 12 by a suitable distance. Through this, the middle portion 11 can use the side surface 111 thereof that protrudes out of each end portion 12 to abut against a surface of the bone defect structure 3 (see FIG. 3) with large undulation.

Figure 17:
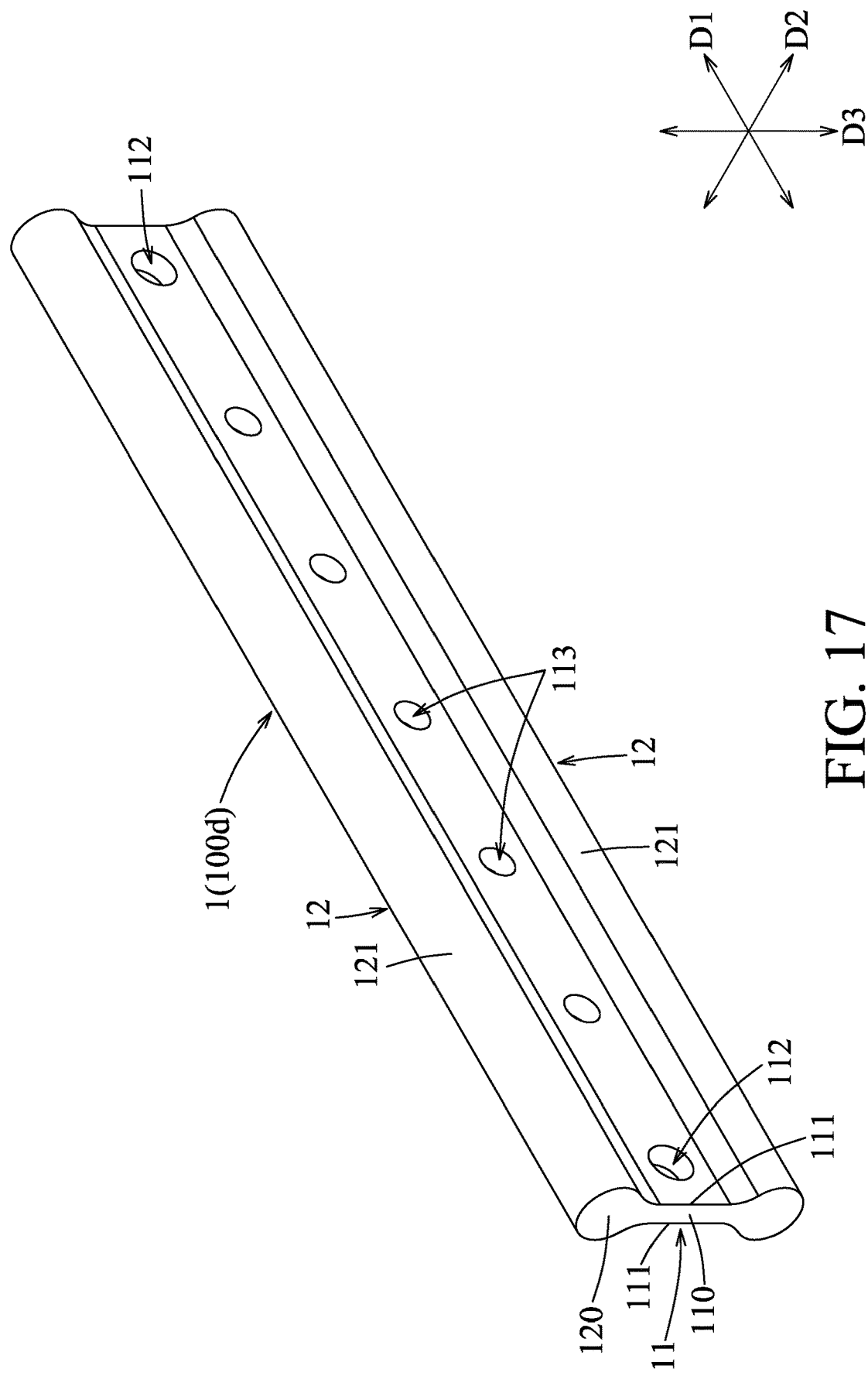
FIG. 17 is a side view of a support bar of a support device according to the seventh embodiment of the present disclosure.

Referring to FIG. 17, the seventh embodiment of the support device (100*d*) of this disclosure is shown to be identical to the first embodiment in structure, but differs in the method of use.

In the first embodiment, after the repair of the bone is completed when the bone powder 6 grows into bone in the space 34, implantation of a dental prosthesis can then be performed. After a long term use, the implant dental prosthesis will almost face the condition of bone resorption at the buccal side 32. This is because there is lack of periodontal ligament like that of a natural tooth around the implant, so that it is unable to stimulate bone proliferation through the body of the ligament. The bone resorption at the buccal side 32 will cause many problems, such as food residues that are not easy to clean, gum inflammation, and even peri-implant inflammation. Thus, in the seventh embodiment, when the gum is healed and a slot is cut on the gum, only the clamping plate 2 (see FIG. 9) is removed, and the support bar 1 is retained at the specific position and is not removed. Through this, the bone resorption at the buccal side 32 can be reduced.

In another implementation of the seventh embodiment, in the step of mounting the support bar 1 (step S2) (see FIG. 4), the middle portion 11 of the support bar 1 of the support device (100*d*) is bored with a plurality of apertures 113 using a tool, such as pliers. The apertures 113 extend through the side surfaces 111 of the middle portion 11, are located between the through holes 112, and are spaced apart from each other along the length direction (D1). The apertures 113 can allow soft tissue to grow therein so as to enhance the connection stability, so that, after the bone covers the support bar 1, it can be firmly connected thereto. In yet another implementation of the seventh embodiment, the end faces 110 and the side surfaces 111 of the middle portion 11 and the cylindrical surfaces 121 and the end faces 120 of the end portions 12 may undergo surface treatment, such as sandblasting or acid etching, to increase the surface roughness thereof so as to improve bone adhesion, so that after the bone covers the support bar 1, it can be firmly connected thereto.

In summary, the support bar 1 of the support device 100~100*d* in each embodiment has the smooth cylindrical surfaces 121 of the end portions 12 supporting the biological membrane 4 to prevent the gum from being pierced by any of the end portions 12 during the healing period thereof, thereby preventing exposure of the support bar 1 from the bone grafting area which may cause failure of the operation. Further, through the configuration of the clamping plate 2, the biological membrane 4 can be conveniently and quickly fixed to the support bar 1 so as to prevent the biological membrane 4 from shaking relative to the support bar 1. In the first embodiment, since the support bar 1 is elongated and can span across the corner portion 341 (see FIG. 3) of the space 34, a single set of the support device 100 can be used to achieve the effect of stably supporting the biological membrane 4, and the convenience of assembly and disassembly of the support device 100 can be enhanced. In the second and third embodiments, since the support bar 1 can be bent to form an inverted U-shape and support the biological membrane 4, the effect of stably supporting the biological membrane 4 can be achieved. In the first to sixth embodiments, since only the middle portion 11 of the support bar 1 is formed with the through holes 112 for extension of the bone screws 5 therethrough, soft tissue can be prevented from growing and adhering to the support bar 1 during the healing period of the gum. Through this, after the gum is healed, a slot is cut on the gum, the clamping plate 2 is first detached from the support bar 1, after which the bone screws 5 are unscrewed, and the support bar 1 can then be conveniently and quickly removed from the gum. In the seventh embodiment, the support bar 1 is retained at the specific position and is not removed to reduce the bone resorption at the buccal side 32. Therefore, the object of this disclosure can indeed be achieved.

In the description above, for the purposes of explanation, numerous specific details have been set forth in order to provide a thorough understanding of the embodiments. It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects, and that one or more features or specific details from one embodiment may be practiced together with one or more features or specific details from another embodiment, where appropriate, in the practice of the disclosure.

While the disclosure has been described in connection with what are considered the exemplary embodiments, it is understood that this disclosure is not limited to the disclosed embodiments but is intended to cover various arrangements included within the spirit and scope of the broadest interpretation so as to encompass all such modifications and equivalent arrangements.

What is claimed is:

1. A support device for supporting a biological membrane, comprising:
    a support bar that is elongated, that extends along a length direction and that has at least one cylindrical surface extending along the length direction for supporting the biological membrane; and
    a clamping plate detachably clamped to said support bar for fixing the biological membrane to said support bar, wherein said support bar includes a middle portion, and at least one end portion formed on one end of said middle portion and having said at least one cylindrical surface,
    wherein said at least one end portion of said support bar includes two end portions formed on two ends of said middle portion that are opposite to each other along a height direction transverse to the length direction,
    wherein said clamping plate includes a main plate body, and two elastic plate bodies respectively bent from two opposite ends of said main plate body for clamping the biological membrane to said cylindrical surfaces of said end portions of said support bar, each of said elastic plate bodies having a free end for pressing the biological membrane against said cylindrical surface of a respective one of said end portions of said support bar, said free ends of said elastic plate bodies being spaced apart from each other along the height direction by a distance which is smaller than a height of said support bar along the height direction, said free end of each of said elastic plate bodies being slidable on said cylindrical surface of the respective one of said end portions of said support bar to urge each of said elastic plate bodies to bend and deform relative to said main plate body.

2. The support device as claimed in claim 1, wherein said support bar is flexible and bendable.

3. The support device as claimed in claim 1, wherein said middle portion of said support bar has two side surfaces opposite to each other along a thickness direction transverse to the length direction and the height direction, said cylindrical surface of each of said end portions of said support bar being connected to and protruding out of said side surfaces.

4. The support device as claimed in claim 3, wherein said middle portion of said support bar has a first thickness extending in the thickness direction smaller than a second thickness of each of said end portions of said support bar extending in the thickness direction.

5. The support device as claimed in claim 4, wherein said first thickness is 0.5 mm, said second thickness is 1 mm, and said cylindrical surface of each of said end portions of said support bar protrudes from a corresponding one of said side surfaces by a distance of 0.25 mm.

6. The support device as claimed in claim 1, wherein each of said end portions of said support bar further has two end faces respectively connected to two opposite ends of said cylindrical surface of a corresponding one of said end portions, said middle portion of said support bar having two end faces opposite to each other along the length direction, each of said end faces of said middle portion being connected between one of said end faces of one of said end portions and a corresponding one of said end faces of the other one of said end portions.

7. The support device as claimed in claim 6, wherein each of said end portions of said support bar is formed with a through passage extending between said end faces.

8. The support device as claimed in claim 6, wherein said middle portion and said end portions of said support bar cooperatively define a through passage that extends between said end faces of said middle portion and between said end faces of each of said end portions.

9. The support device as claimed in claim 1, wherein said support bar has a height extending in the height direction smaller than or equal to 3 mm, and a thickness extending in a thickness direction transverse to the length direction and the height direction larger than or equal to 1 mm.

\* \* \* \* \*